United States Patent
Raue et al.

Patent Number: 5,502,171
Date of Patent: Mar. 26, 1996

[54] PROCESS FOR THE PREPARATION OF DYESTUFFS

[75] Inventors: Roderich Raue, Leverkusen; Alfred Brack, Odenthal; Karl-Heinrich Lange, Leverkusen, all of Germany

[73] Assignee: Bayer Aktiengesellschaft, Leverkusen, Germany

[21] Appl. No.: 442,049

[22] Filed: May 16, 1995

Related U.S. Application Data

[62] Division of Ser. No. 311,831, Sep. 23, 1994, which is a continuation of Ser. No. 48,024, Apr. 15, 1993, abandoned, which is a continuation-in-part of Ser. No. 874,674, Apr. 27, 1992, abandoned, which is a continuation-in-part of Ser. No. 665,632, Mar. 6, 1991, abandoned.

[30] Foreign Application Priority Data

Mar. 15, 1990 [DE] Germany .......................... 40 08 263.6

[51] Int. Cl.$^6$ .................................................. C09B 41/00
[52] U.S. Cl. ........................... 534/579; 534/580; 534/581
[58] Field of Search ................................... 534/579, 580, 534/581

[56] References Cited

U.S. PATENT DOCUMENTS 2,978,290   4/1961   Bossard et al. .
4,432,897   2/1984   Furstenworth .

FOREIGN PATENT DOCUMENTS 1069563   11/1959   Germany .
2017134   10/1979   United Kingdom .

OTHER PUBLICATIONS

Patent Abstracts of Japan, vol. 6, No. 177 (C–124) (1055), Sep. 11, 1982; JP-A-57-91975, "Water–Soluble Heterocyclic Azo Compound and Its Application", Doujin Kagaku Kenkyusho K.K., Jun. 8, 1982.

*Primary Examiner*—Johann Richter
*Assistant Examiner*—John D. Peabody
*Attorney, Agent, or Firm*—William C. Gerstenzang; Sprung Horn Kramer & Woods

[57] ABSTRACT

Dyestuffs of the formula

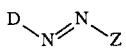

in which
  D is the radical of an aromatic or heterocyclic diazo component and
  Z is the radical of an aromatic or heterocyclic coupling component, are obtained in an ecologically advantageous manner by reacting an aromatic or heterocyclic diazo components of the formula

D—NH$_2$ and a coupling component of the formula

H—Z$_1$ with a nitrite, in the presence of $CO_2$ at a pressure of 5–100 at. The process is suitable in particular for the preparation of concentrated dyestuff solutions, because expensive operations, such as, for example, pressure permeation and reverse osmosis, can be omitted.

12 Claims, No Drawings

PROCESS FOR THE PREPARATION OF DYESTUFFS

This application is a divisional of application Ser. No. 08/311.831, filed on Sep. 23, 1994, now pending which is a continuation of Ser. No. 08/048.024, filed on Apr. 15, 1993, now abandoned which is a continuation-in-part of Ser. No. 07/874,674, filed on Apr. 27, 1992, now abandoned, which is a continuation-in-part of Ser. No. 07/665,632, filed on Mar. 6, 1991, now abandoned The present invention relates to a process for the preparation of dyestuffs of the general formula

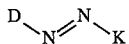  (I)

in which
D is the radical of an aromatic or heterocyclic diazo component and
K is the radical of an aromatic or heterocyclic coupling component, or is the radical of an active methylene compound, in which an aromatic or heterocyclic diazo component of the formula

D—NH$_2$  (II)

and a coupling component of the formula

H—K  (III)

are reacted in an aqueous medium with a nitrite in the presence of $CO_2$ at a pressure of 5–100 bar at a temperature of 0°–125° C.,
and further relates to a process for the preparation of dyestuffs of the general formula

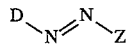  (XVI)

in which
D is the radical of an aromatic or heterocyclic diazo component and
Z is the radical of an arylamino group or is the radical of a heterocyclylimino group of the formula —N=Het  (XVII)

in which
Het is a heterocyclic diradical in which an aromatic or heterocyclic diazo component of the formula

D—NH$_2$  (II)

and a component of the formula

H—Z$_1$  (XVIII)

in which
Z$_1$ is the radical of an arylamino or hetarylamino group are reacted in an aqueous medium with a nitrite in the presence of $CO_2$ at a pressure of 5–100 bar at a temperature of 0°–125° C.

A suitable reaction medium is water, if desired in a mixture with organic solvents which are completely or partially miscible with water.

Compounds with activated methylene groups used as coupling compounds HK can be selected from β-diketones, such as benzoylacetone, 1,3-cyclohexanedione and 1,3-perinaphthalindanedione; beta-keto esters, such as ethyl acetoacetate, diethyl malonate, phenylacetoacetate, methyl-4,4,4-trifluoroacetoacetate, and methyl-p-nitrobenzoylacetate, beta-keto amides, such as acetoacet-4'-chloroanilide, acetoacetotoluidide, benzoylacet-3'-methoxyanilide, benzoylacet-α,β-naphthylamide, and N,N'-ditolylmalonamide; beta-keto nitriles, such as benzoylacetonitrile, 2'-thenoylacetonitrile, anisoylacetonitrile, 1-naphthoylacetonitrile, and p-nitrocinnamoylacetonitrile; anilides of cyanoacetic acid, such as 2-cyanoacetanilide, 2-cyano-p-acetanisidide, and 2-cyano-4'-nitroacetanilide; heterocyclic beta-keto amides, such as barbituric acid and N-substituted barbituric acids; and β-imino amides, such as 1-phenyl-3-methylpyrazoyl-5-one, 1-hydroxymethyl-3-methylpyrazol- 5-one, 2-iminobarbituric acid, and 1-(α -naphthyl)-3-methyl-pyrazol-5-one.

Further HK can be selected from 1-phenyl-5-pyrazolone; 3-methyl-5-pyrazolone; 3-ethyl-5-pyrazolone; 1-phenyl-3-ethoxycarbonyl-5-pyrazolone; 1-phenyl-3-butoxycarbonyl-5-pyrazolone; 1-phenyl-3-phenoxycarbonyl-5-pyrazolone; 1-phenyl- 3-carbamoyl-5-pyrazolone; 1-phenyl-3-methylcarbamoyl-5-pyrazolone; 1-phenyl-3-dimethylcarbamoyl-5-pyrazolone; 1-phenyl-3-phenylcarbamoyl-5-pyrazolone; 1-phenyl-3-(2-hydroxyethyl-carbamoyl)- 5-pyrazolone; 2-methylindole; 5-bromo-2-methylindole; 2-hydroxy-carbazole; 3-hydroxydibenzofurane; 5-hydroxyquinoline; 8-hydroxyquinoline; 5-hydroxyisoquinoline; 2,4-dihydroxyquinoline; 1-(m-nitrophenyl)-3-methyl-5-pyrazolone; 1-(p-nitrophenyl)-3-methyl-5-pyrazolone; 1,2,3,4-tetrahydro- 6-methoxyquinoline; 1,2,3,4-tetrahydro-7-methylquinoline; 1,2,3,4-tetrahydro-1-methylquinoline; 1,2,3,4-tetrahydro- 1-(2-hydroxyethyl)quinoline; 3,4-dihydro-2H-1,4-benzoxazine(benzomorpholine); 4-ethyl-3,4-dihydro-2H-1,4-benzoxazine; 4-(2-cyanoethyl)-3,4-dihydro-2H-1,4-benzoxazine julolidine; 2-acetamidothiophene, 2-benzamidothiophene, 2-dimethylaminothiazole; indazol-6-one, 2-phenylindole; 1-dimethylaminomethyl-3-methylpyrazol-5-one; and 1,3,3-trimethyl-2-methylene-2,3-dihydroindole.

Preference is given to heterocyclic compounds containing activated methylene groups.

Suitable solvents are methanol, ethanol, propanol, isopropanol, isoamyl alcohol, ethylene glycol, methylglycol, ethylglycol, butylglycol, ethylene glycol dimethyl ether, ethylene glycol diethyl ether, diethylene glycol dimethyl ether, glycol diacetate, methylglycol acetate, ethylglycol acetate, butylglycol acetate, propylene glycol, propylene glycol monomethyl ether, propylene glycol monoethyl ether, propylene glycol dimethyl ether, propylene glycol diethyl ether, propylene glycol acetate, triacetin, acetonitrile, tetrahydrofuran, dioxane, dimethylformamide and N-methylpyrrolidone.

The reaction can be carried out at 0°–125° C. The preferred reaction temperature is in general 0°–100° C., especially 0°–70° C., very especially 30°–40° C.

At atmospheric pressure, no reaction with $CO_2$ takes place.

Surprisingly, it has been found that when the $CO_2$ pressure is increased to more than 5 bar the diazotization and simultaneous coupling reaction to give azo dyestuffs takes place. The preferred pressure range is 25–65 bar.

Examples of suitable nitrites are sodium nitrite, potassium nitrite, methyl nitrite, isopropyl nitrite, amyl nitrite, glycol nitrite and pentaerythritol nitrite or diethylene glycol nitrite. Preferably the reaction is carried out during a time of 10 minutes to 24 hours. Until now, the preparation of azo dyestuffs has been carried out by diazotization of the aromatic or heterocyclic amines in mineral acid solution, addition of the diazonium salt solution to the solution of the coupling component, and coupling by the addition of acid-binding agents. DE-AS (German Published Specification)

2,139,311 has disclosed the preparation of azo dyestuffs by means of a one-step diazotization and coupling. EP 42,556 describes the preparation of cationic alkylaryl hydrazone dyestuffs and colour bases thereof by reaction of aromatic amines and indoline compounds with a substance releasing nitrous acid in the presence of an acid. In any case, an inorganic or organic acid was used until now for the diazotization which has to be neutralized in the coupling reaction which follows. This leads to the formation of inorganic salts. When the dyestuff is isolated, these inorganic salts enter the wastewater and represent a pollution which is unacceptable in many cases. In a mixture with the prepared dyestuff, inorganic salts often have an adverse effect on the solubility. To prepare stable dyestuff solutions, these salts have to be removed by expensive processes, for example pressure permeation or reverse osmosis. The new preparation process according to the invention avoids all these disadvantages.

In particular the process of the present invention is concerned with the preparation of dyestuffs of the formula (I) in which D is the radical of a substituted or unsubstituted aromatic diazo component containing 6–10 carbon atoms or is the radical of a substituted or unsubstituted 5- or 6-membered heterocyclic diazo component containing 1 to 3 hetero atoms selected from N, O, S and optionally containing one or two fused 5- and/or 6-membered substituted or unsubstituted carbocyclic rings and K is the radical of a substituted or unsubstituted aromatic coupling component containing 6 to 10 carbon atoms or is a radical of a substituted or unsubstituted 5- or 6-membered heterocyclic coupling component or heterocyclic component containing an active methylene group and containing in each case one or two hetero atoms selected from N, O, S and optionally containing in each case one or two fused 5- and/or 6-membered substituted or unsubstituted carbocyclic rings, and as far as substituents for the substituted aromatic diazo component, the substituted 5- or 6-membered heterocyclic diazo component, the substituted aromatic coupling component, the substituted 5- or 6-membered heterocyclic or heterocyclic methylene active coupling component or the substituted carbocyclic rings are concerned, they are selected from the series comprising $C_1$–$C_4$-alkyl, $C_6$–$C_{10}$-aryl, $C_1$–$C_4$-alkoxy, $C_1$–$C_4$-alkoxycarbonyl, $C_1$–$C_4$-alkylcarbonyloxy, cyano, $C_1$–$C_4$-(di)alkylamino, $C_1$–$C_4$-(di)alkylaminocarbonyl, $C_1$–$C_4$-alkylcarbonylamino, hydroxy, halogen, $C_1$–$C_4$-alkylcarbonyl, $C_1$–$C_4$-alkylsulphonyl, $C_1$–$C_4$-(di)alkylaminosulphonyl, $C_1$–$C_4$-alkylsulphonyloxy, nitro, $C_6$–$C_{10}$-(di)arylamino, $C_1$–$C_4$-alkyl-$C_6$–$C_{10}$-arylamino, phenylsulphonyl, phenylazo, benzothiazolyl, 1,2,4-oxadiazolyl, morpholino, piperidino, piperazino, pyrrolidino, $C_1$–$C_4$-alkylmercapto and $C_6$–$C_{10}$-arylmercapto.

More particularly the process of the present invention is concerned with the preparation of dyestuffs of the formula (I) in which D is the radical of a substituted or unsubstituted aromatic diazo component containing 6 to 10 carbon atoms or is the radical of a heterocyclic diazo component selected from the the group consisting of substituted and unsubstituted, benzo-fused and non-benzo-fused thiazols, isothiazols, thiadiazols, oxazols, imidazols and triazols and K is the radical of a substituted or unsubstituted aromatic coupling component containing 6 to 10 carbon atoms or is the radical of a substituted or unsubstituted 5- or 6-membered heterocyclic coupling component or heterocyclic component containing an active methylene group and containing in each case one or two hetero atoms selected from N, O, S and optionally containing in each case one or two fused substituted or unsubstituted benzene rings, and as far as substituents for the substituted aromatic diazo components the substituted heterocyclic diazo components the substituted aromatic coupling components, the substituted heterocyclic or heterocyclic methylene active coupling components and the substituted benzene rings are concerned, they are selected from the series comprising $C_1$–$C_4$-alkyl, $C_6$–$C_{10}$-aryl, $C_1$–$C_4$-alkoxy, $C_1$–$C_4$-alkoxycarbonyl, $C_1$–$C_4$-alkylcarbonyloxy, cyano, $C_1$–$C_4$-(di)alkylamino, $C_1$–$C_4$-(di)alkylaminocarbonyl, $C_1$–$C_4$-alkylcarbonylamino, hydroxy, halogen, $C_1$–$C_4$-alkylcarbonyl, $C_1$–$C_4$-alkylsulphonyl, $C_1$–$C_4$(di)alkylaminosulphonyl, $C_1$–$C_4$-alkylsulphonylamino, $C_1$–$C_4$-alkoxysulphonyl, $C_1$–$C_4$-alkylsulphonyloxy and nitro.

Most particularly the process of the present invention is concerned with the preparation of azo dyestuffs of the formula (I) in which K is a radical of the formula

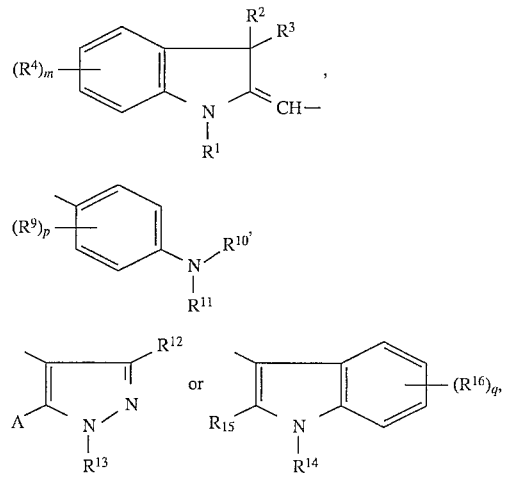

in which $R^1$ represents hydrogen or alkyl having 1–4 carbon atoms which can be substituted by halogen, hydroxyl, cyano, $C_1$–$C_4$-alkoxy, $C_1$–$C_4$-alkylcarbonyloxy, phenoxy, phenyl, hydroxycarbonyl or $C_1$–$C_4$-alkylsulphonyl, $R^2$ and $R^3$ independently of one another, represent methyl or ethyl and $R^4$ represents hydrogen, halogen, alkyl or alkoxy having 1–4 C atoms, benzyl, benzyloxy, phenyl or phenoxy radicals each of which in turn can be substituted by halogen, alkyl or alkoxy of 1–4 C atoms, acetyl, benzoyl or carboxylic esters having 1–4 C atoms, m represents 1 or 2, $R^9$ represents hydrogen, alkyl or alkoxy having 1–4 C atoms, acylamino having 1–4 C atoms, a hydroxyl or carboxyl group, $R^{10}$ and $R^{11}$, independently of one another, represent hydrogen or alkyl having 1–4 carbon atoms which can be substituted by halogen, hydroxyl, cyano, $C_1$–$C_4$-alkoxy, $C_1$–$C_4$-carbonyloxy, phenoxy or phenyl, or $R^{10}$ and $R^{11}$ together with the nitrogen atom to which they are attached represent the remaining members of a 5- or 6-membered heterocyclic ring which can furthermore contain one additional hetero atom selected from N, O and S, $R^{10}$ furthermore represents a phenyl radical which in turn can be substituted by halogen, alkyl or alkoxy of 1–4 C atoms, $R^{11}$ furthermore represents an alkylene radical which forms a partially hydrogenated 5- or 6-membered heterocyclic ring by a ring closure with the benzene ring, p represents 1, 2 or 3.

$R^{12}$ represents methyl, phenyl, carboxamide or carboxylic alkyl esters of 1–4 C atoms, and $R^{13}$ represents hydrogen, an amidino group or a phenyl radical which is unsubstituted or substituted by 1–3 halogens, alkyl, alkoxy, carboxyl, carboxamido, sulpho or sulphonamido groups, A represents hydroxyl or amino $R^{14}$ represents hydrogen, alkyl of 1–4 C atoms or phenyl, $R^{15}$ represents hydrogen, alkyl of 1–4 C atoms or a phenyl radical which can be unsubstituted or substituted by 1–3 halogens, alkyl or alkoxy radicals of 1–4 C atoms, and $R^{16}$ represents halogen, alkyl or alkoxy of 1–4 C atoms, q is 0, 1 or 2, and and D is a radical of the formula

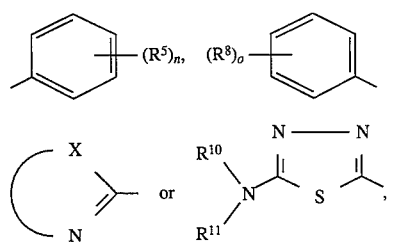

in which $R^5$ represents hydrogen, halogen, alkyl or alkoxy having 1–4 C atoms, benzyl, benzyloxy, phenyl or phenoxy radicals each of which in turn can be substituted by halogen, alkyl or alkoxy of 1–4 C atoms, acetyl, benzoyl or carboxylic esters having 1–4 C atoms or represents phenylazo or together with the benzene ring a tetraline, naphthalene or benzodioxane ring system and n represents 1 or 2, $R^8$ represents hydrogen, halogen, alkyl, alkoxy having 1–4 C atoms, aminoalkyl, dialkylaminoalkyl, trialkylammonium groups, benzyl, benzyloxy, phenyloxy radicals, acetyl, benzoyl, carboxylic esters having 1–4 C atoms, carboxamide, carboxyl, nitro, sulphonamide or the sulpho group.

o represents 1 or 2 and

X represents the remaining members of a thiazole, isothiazole, benzothiazole, 1,2,4-triazole or 1,3,4-thiadiazole radical.

Further the process of the present invention is in particular concerned with the preparation of dyestuffs of the formula (XVI)

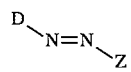 (XVI)

in which

D is the radical of a substituted or unsubstituted aromatic diazo component containing 6–10 carbon atoms or is the radical of a substituted or unsubstituted 5- or 6-membered heterocyclic diazo component containing 1 to 3 hetero atoms selected from N, O, S and optionally containing one or two fused 5- and/or 6-membered substituted or unsubstituted carbocyclic rings, Z is the radical of a substituted or unsubstituted $C_6$–$C_{10}$-arylamino group or is the radical of a substituted or unsubstituted heterocyclylimino group of the formula $$-N=Het \qquad (XVII)$$

in which

Het is the diradical of a substituted or unsubstituted saturated or partially unsaturated 5- or 6-membered heterocyclic ring containing 1 to 3 hetero atoms selected from N, O, S and optionally containing one or two fused 5-and/or 6-membered substituted or unsubstituted carbocyclic rings, in which an aromatic or heterocyclic diazo component of the formula (II)

in which

D has the above given meaning is reacted with a component of the formula (XVIII) in which $Z_1$ is the radical of a substituted or unsubstituted $C_6$–$C_{10}$-arylamino group or is the radical of a substituted or unsubstituted 5- or 6-membered hetarylamino group containing 1 to 3 hereto atoms within the hetaryl moiety selected from O, N, S and optionally containing one or two fused 5- and/or 6-membered substituted or unsubstituted carbocyclic rings and as far as substituents for the substituted aromatic diazo component, the substituted 5- or 6-membered heterocyclic diazo component, the aryl part of the substituted $C_6$–$C_{10}$-arylamino groups in the definition of Z and $Z_1$, the heterocyclyl part of the heterocyclylimino group, the hetaryl part of the hetarylamino group, or the substituted carbocyclic rings are concerned, they are selected from the series comprising $C_1$–$C_4$-alkyl, $C_6$–$C_{10}$-aryl, $C_1$–$C_4$-alkoxy, $C_1$–$C_4$-alkoxycarbonyl, $C_{-C4}$-alkylcarbonyloxy, cyano, $C_1$–$C_4$-(di)alkylamino, $C_1$–$C_4$-(di)alkylaminocarbonyl, $C_1$–$C_4$-alkylcarbonylamino, hydroxy, halogen, $C_1$–$C_4$-alkylcarbonyl, $C_1$–$C_4$-alkylsulphonyl, $C_1$–$C_4$-(di)alkylaminosulphonyl, $C_1$–$C_4$-alkylsulphonylamino, $C_1$–$C_4$-alkoxysulphonyl, $C_1$–$C_4$-alkylsulphonyloxy, nitro, $C_6$–$C_{10}$-(di)arylamino, $C_1$–$C_4$-alkyl-$C_6$–$C_{10}$-arylamino, phenylsulphonyl, phenylazo, benzothiazolyl, 1,2,4-oxadiazolyl, morpholino, piperidino, piperazino, pyrrolidino, $C_1$–$C_4$-alkylmercapto and $C_6$–$C_{10}$-arylmercapto and as far as the amino part of the substituted $C_6$–$C_{10}$-arylamino group in the definition of Z and $Z_1$ is concerned, it can be substituted by substituted or unsubstituted $C_1$–$C_8$-alkyl, $C_2$–$C_4$-alkylen, substituted or unsubstituted $C_1$–$C_4$-alkyl-$C_6$–$C_{10}$-aryl.

Further the process of the present invention is more particularly concerned with the preparation of dyestuffs of the formula (XVI), in which D is the radical of a substituted or unsubstituted aromatic diazo component containing 6 to 10 carbon atoms or is the radical of a heterocyclic diazo component selected from the the group consisting of substituted and unsubstituted, benzo-fused and none benzo-fused thiazols, isothiazols, thiadiazols, oxazols, imidazols and triazols and Z is the radical of the formula

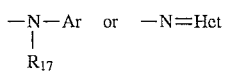

in which
- Ar is in each case substituted or unsubstituted phenyl or naphthyl,
- $R_{17}$ represents hydrogen, unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen, unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy,
- Het represents the diradical of a partially unsaturated 5-membered heterocyclic ring, containing 1 to 3 hetero atoms selected from N, O, S and optionally containing one fused benezene ring which can be substituted or unsubstituted and the heterocyclic ring is unsubstituted or substituted one to three-times by identical or different substituents selected from the group consisting of unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen, unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy, $C_1$–$C_4$-(di)alkylamino, $C_6$–$C_{10}$-(di)arylamino, $C_1$–$C_4$-alkyl-$C_6$–$C_{10}$-arylamino, morpholino, piperidino, piperazino, pyrrolidino, $C_1$–$C_4$-alkylmercapto or $C_6$–$C_{10}$-arylmercapto, in which an aromatic or heterocyclic diazo component of the Formula (II), in which D has the above given meaning, is reacted with a component of the formula (XVIII) in which
- $Z_1$ is the radical of the formula

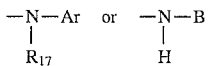

in which Ar and $R_{17}$ have the above mentioned meaning, and B is the radical of a 5-membered, unsaturated heterocyclic ring, containing 1 to 3 hetero atoms selected from N, O, S and optionally containing one fused benzene ring, which can be substituted or unsubstituted and the heterocyclic ring is unsubstituted or substituted one to three times by identical or different substituents selected from the group consisting of of unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy, $C_1$–$C_4$-(di)alkylamino, $C_6$–$C_{10}$-(di)arylamino, $C_1$–$C_4$-alkyl-$C_6$–$C_{10}$-arylamino, morpholino, piperidino, piperazino, pyrrolidino, $C_1$–$C_4$-alkylmercapto or $C_6$–$C_{10}$-arylmercapto and and as far as substituents for the substituted aromatic diazo components and the substituted phenyl and naphthyl radicals in the definition of Z and $Z_1$ and the fused benzene rings in the defintions of Het and B are concerned, they are selected from the series comprising $C_1$–$C_4$-alkyl, $C_6$–$C_{10}$-aryl, $C_1$–$C_4$-alkoxy, $C_1$–$C_4$-alkoxycarbonyl, $C_1$–$C_4$-alkylcarbonyloxy, cyano, $C_1$–$C_4$-(di)alkylamino, $C_1$–$C_4$-(di)alkylaminocarbonyl, $C_1$–$C_4$-alkylcarbonylamino, hydroxy, halogen, $C_1$–$C_4$-alkylcarbonyl, $C_1$–$C_4$-alkylsulphonyl, $C_1$–$C_4$-(di)alkylaminosulphonyl, $C_1$–$C_4$-alkylsulphonylamino, $C_1$–$C_4$-alkoxysulphonyl, $C_1$–$C_4$-alkylsulphonyloxy and nitro.

The process of the present invention is especially concerned with the preparation of dyestuffs of the formula (XVI) in which
- D is the radical of a substituted or unsubstituted aromatic diazo component containing 6 to 10 carbon atoms or is the radical of a heterocyclic diazo component selected from the the group consisting of substituted and unsubstituted, benzo-fused and non-benzo-fused thiazols, isothiazols, thiadiazols, oxazols, imidazols and triazols and
- Z is the radical of the formula

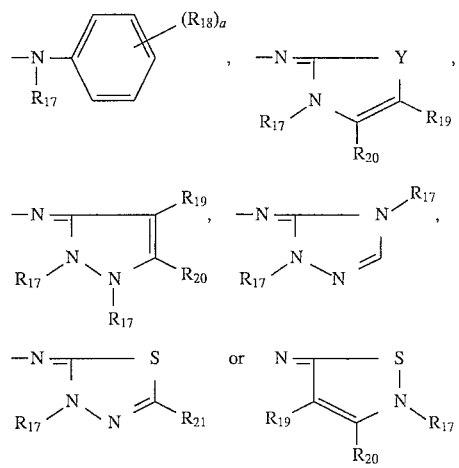

in which
- Y represents —S—, —O— or

- $R_{17}$ represents hydrogen, unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen, unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy,
- $R_{18}$ represents $C_1$–$C_4$-alkyl, $C_1$–$C_4$-alkoxy, halogen, nitro, cyano, $C_1$–$C_4$-alkylsulphonyl, phenylsulphonyl, $C_1$–$C_4$-alkylcarbonylamino, phenylazo, benzothiazolyl or 1,2,4-oxadiazolyl
- a represents 0, 1, 2 or 3,
- $R_{19}$ and $R_{20}$ either represent hydrogen or together represent the remaining members of a fused benzene ring and
- $R_{21}$ represents $C_1$–$C_4$-(di)alkylamino, $C_6$–$C_{10}$-(di)arylamino, $C_1$–$C_4$-alkyl-$C_6$–$C_{10}$-arylamino, morpholino, piperidino, piperazino, pyrrolidino, $C_1$–$C_4$-alkylmercapto or $C_6$–$C_{10}$-arylmercapto and in which an aromatic or heterocyclic diazo component of the formula (II), in which D has the above given meaning, is reacted with a component of the formula (XVIII) in which
- $Z_1$ is the radical of the formulae

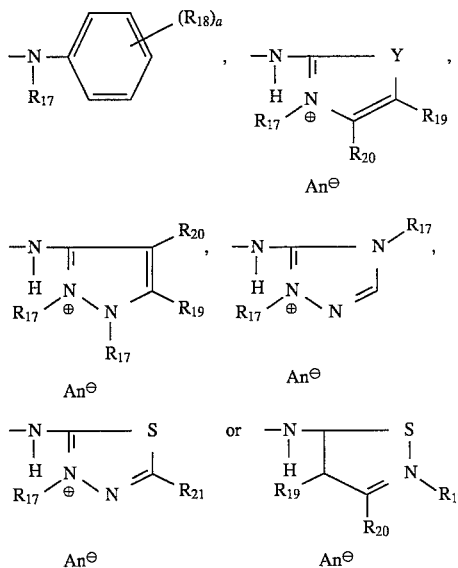

in which

Y, $R_{17}$, $R_{18}$, $R_{19}$, $R_{20}$, $R_{21}$ and a have the above given meaning and $An^\ominus$ represents an anion selected from the series comprising $Cl^\ominus$, $CH_3OSO_2O^\ominus$, $J^\ominus$, $Br^\ominus$, $CH_3COO^\ominus$.

The following dyestuff groups (IV), (VII), (XXI), (X), (XII), (XIV) and (XIX) can be prepared, for example, by the process according to the invention in an aqueous medium with a substance releasing nitrous acid in the presence of $CO_2$ at a pressure of 5–100 bar at a temperature of 0°–125° C.:

Colour bases of the formula

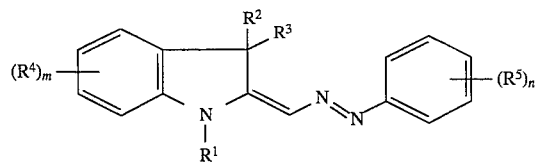

in which $R^1$ represents hydrogen or alkyl having 1–4 carbon atoms which can be substituted by halogen, hydroxyl, cyano, $C_1$–$C_4$-alkoxy, $C_1$–$C_4$-alkylcarbonyloxy, phenoxy, phenyl, hydroxycarbonyl or $C_1$–$C_4$-alkylsulphonyl, $R^2$ and $R^3$, independently of one another, represent methyl or ethyl and $R^4$ and $R^5$, independently of one another, represent hydrogen, halogen, alkyl or alkoxy having 1–4 C atoms, benzyl, benzyloxy, phenyl or phenoxy radicals each of which in turn can be substituted by halogen, alkyl or alkoxy of 1–4 C atoms, acetyl, benzoyl or carboxylic esters having 1–4 C atoms or $R^5$ represents phenylazo or together with the benzene ring a tetraline, naphthalene or benzodioxane ring system and m and n, independently of one another, represent 1 or 2, are prepared by reacting an aromatic amine of the formula

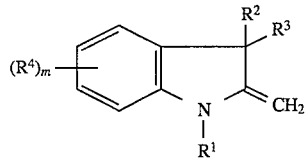

and a compound of the formulae

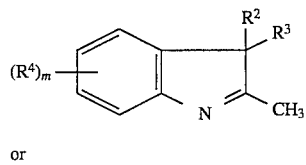

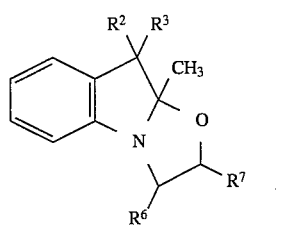

in which $R^1$ to $R^5$, m and n have the abovementioned meaning, and $R^6$ and $R^7$ independently of one another, represent hydrogen, alkyl, alkoxy of 1–4 carbon atoms, phenyl or phenoxy.

Dyestuffs of the formula

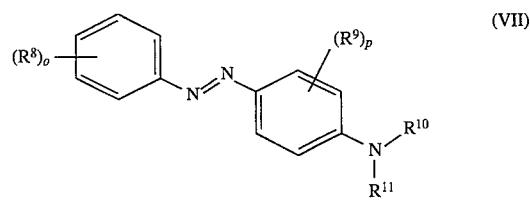

in which $R^8$ represents hydrogen halogen alkyl alkoxy having 1–4 C atoms, aminoalkyl, alkylaminoalkyl, dialkylaminoalky, trialkylammonium groups, benzyl, benzyloxy, phenyloxy radicals, acetyl, benzoyl, carboxylic esters having 1–4 C atoms, carboxamide, carboxyl, nitro, sulphonamide or the sulpho group $R^9$ represents hydrogen, alkyl or alkoxy having 1–4 C atoms, acylamino having 1–4 C atoms, a hydroxyl or carboxyl group, $R^{10}$ and $R^{11}$, independently of one another, represent hydrogen or alkyl having 1–4 carbon atoms which can be substituted by halogen, hydroxyl, cyano, $C_1$–$C_4$-alkoxy, $C_1$–$C_4$-carbonyloxy, phenoxy or phenyl, or $R^{10}$ and $R^{11}$ together with the nitrogen atom to which they are attached represent the remaining members of a 5- or 6-membered heterocyclic ring which can furthermore contain one additional hetero atom Selected from N, O and S, $R^{10}$ furthermore represents a phenyl radical which in turn can be substituted by halogen, alkyl or alkoxy of 1–4 C atoms, $R^{11}$ furthermore represents a bivalent alkylene radical which forms a partially hydrogenated 5- or 6-membered heterocyclic ring which is fused with the adjacent phenyl to form a bicyclic structure, o represents 1 or 2, and p represents 1, 2 or 3, are prepared by reacting an aromatic amine of the formula

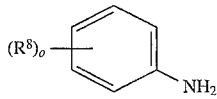   (VIII)

with an aromatic amine of the formula

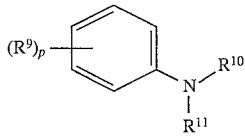   (IX)

in which $R^8$–$R^{11}$ and o and p have the abovementioned meaning.

Compounds of the formula

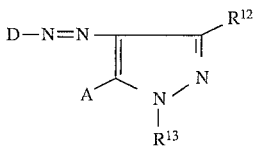   (XXI)

in which

D is a phenyl radical which is unsubstituted or substituted by one or two substituents selected from the series comprising halogen, $C_1$–$C_4$-alkoxy, $C_1$–$C_4$-(di)alkylamino, $C_1$–$C_4$-(di)alkylaminoalkyl, $C_1$–$C_4$-trialkylammonium, benzyl, benzyloxy, phenyloxy, acetyl, benzoyl, $C_1$–$C_4$-alkoxycarbonyl, $C_1$–$C_4$(di)alkylaminocarbonyl, carboxyl, nitro, $C_1$–$C_4$-alkylsulphonyl and sulphonic acid or is a heterocyclic radical selected from the group of substituted and unsubstituted thiazoles, benzothiazoles, isothiazoles, benzoisothiazoles, triazoles, thiadiazoles, imidazoles, benzoimidazoles, oxazoles and benzoxazoles, and the substituents for the mentioned heterocyclic radicals are selected from the series comprising $C_1$–$C_4$-alkyl, $C_1$–$C_4$-alkoxy, $C_1$–$C_4$-alkoxycarbonyl, $C_1$–$C_4$-(di)alkylamino, $C_6$–$C_{10}$-(di)arylamino and $C_1$–$C_4$-alkyl-$C_6$–$C_{10}$-arylamino, $R^{12}$ represents methyl, phenyl, carboxamide or carboxylic alkyl esters of 1–4 C atoms, and $R^{13}$ represents hydrogen, an amidino group or a phenyl radical which is unsubstituted or substituted by 1–3 halogens, alkyl, alkoxy, carboxyl, carboxamido, sulpho or sulphonamido groups, A represents hydroxyl or amino and are prepared by reacting an amine of the formula

D—NH$_2$ in which

D has the above given meaning with a pyrazolone compound of the formula

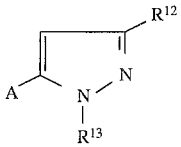   (XXII)

in which $R^{12}$, $R^{13}$ and A have the above given meaning.

Dyestuffs of the formula

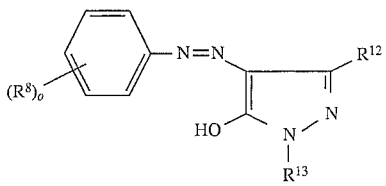   (X)

in which $R^8$ and o have the same meaning as in formula VII, $R^{12}$ represents methyl, phenyl, carboxamide or carboxylic alkyl esters of 1–4 C atoms, and $R^{13}$ represents hydrogen, an amidino group or a phenyl radical which is unsubstituted or substituted by 1–3 halogens, alkyl, alkoxy, carboxyl, carboxamido, sulpho or sulphonamido groups, are prepared by reacting aromatic amines of the formula

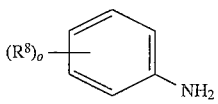   (VIII)

with pyrazolone compounds of the formula

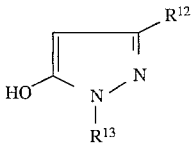   (XI)

in which $R^{12}$ and $R^{13}$ have the abovementioned meaning.

Dyestuffs of the formula

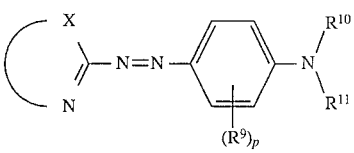   (XII)

in which

X represents the remaining members of a thiazole, isothiazole, benzothiazole, 1,2,4-triazole or 1,3,4-thiadiazole radical and $R^9$, $R^{10}$, $R^{11}$ and p have the same meaning as in formula VII are prepared by reacting heterocyclic amines of the general formula

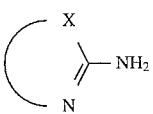   (XIII)

in which

X has the same meaning as in formula XII with aromatic amines of the formula

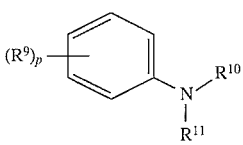   (IX)

Dyestuffs of the general formula

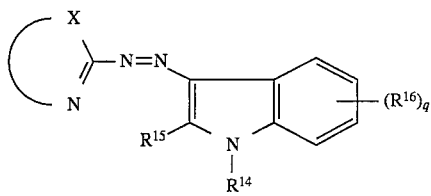

in which

R¹⁴ represents hydrogen, alkyl of 1–4 C atoms or phenyl,

R¹⁵ represents hydrogen, alkyl of 1–4 C atoms or a phenyl radical which can be unsubstituted or substituted by 1–3 halogens, alkyl or alkoxy radicals of 1–4 C atoms, and R¹⁶ represents halogen, alkyl or alkoxy of 1–4 C atoms, q is 0, 1 or 2, and X has the same meaning as in formula XII, are prepared by reacting heterocyclic amines of the formula

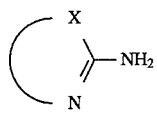

with indole compounds of the formula

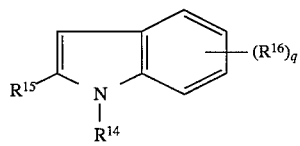

in which

R¹⁴, R¹⁵, R¹⁶ and q have the same meaning as in formula XIV.

Compounds of the formula

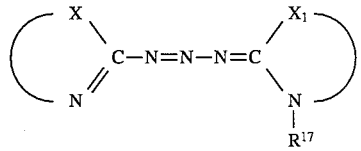

in which

X represents the remaining members of a thiazole, isothiazole, benzothiazole, 1,2,4-triazole or 1,3,4-thiadiazole, X₁ represents the remaining members of a thiazoline, isothiazoline, benzothiazoline, 1,2,4-triazoline, 1,3,4-thiadiazoline radical, R¹⁷ hydroxyl, $C_1$–$C_4$-alkyl, which can be unsubstituted or substituted by cyano, $C_1$–$C_4$-(di)alkylaminocarbonyl, hydroxyl, $C_1$–$C_4$-alkoxy, carboxyl, $C_1$–$C_4$-alkoxycarbonyl, $C_1$–$C_4$-alkylsulphonyl are prepared by reacting a heterocyclic amine of the formula

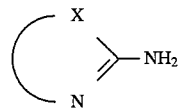

in which X has the above given meaning with a heterocylic ammonium compound of the formula

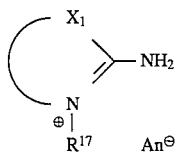

in which

X₁ and R¹⁷ have the above given meaning and An⁻ represents an anion selected from the series comprising Cl⁻, $CH_3OSO_2O^-$, J⁻, Br⁻, $CH_3COO^-$.

Examples of suitable aromatic compounds of the formula V and VIII are aniline, 2-methylaniline, 4-methylaniline, 2,4-dimethylaniline, 3-methylaniline, 4-chloroaniline, 2-chloroaniline, 4-anisidine, 2-anisidine, 4-phenetidine, 2-phenetidine, ethyl 4-aminobenzoate, 4-aminodiphenyl ether, 4-aminophenyl benzyl ether, 4-aminophenyl 4'-chlorobenzyl ether, 4-aminophenyl 4'-methoxybenzyl ether, 4-aminoazobenzene, 4-β-hydroxyethoxyaniline, 4-β-methoxyethoxyaniline, 4-hydroxyethoxyethoxyaniline, 4-β-hydroxy-n-propoxyaniline, 4-β-hydroxy-γ-chloropropoxyaniline, 4-aminocatechol dimethyl ether, 4-aminobenzodioxane, 4-nitroaniline, 2-chloro-4-nitroaniline, 2-bromo-4-nitroaniline, 4-aminobenzenesulphonic acid, 3-aminobenzenesulphonic acid, 2-aminobenzenesulphonic acid, 3-chloro- 4-aminobenzenesulphonic acid, 2-amino-5-chlorobenzenesulphonic acid, 4-aminobenzenesulphonamide, 4-aminobenzoic acid, 3-aminobenzoic acid, 2-aminobenzoic acid.

Examples of suitable coupling components of the formula VIa, b or c are 2,3,3-trimethyl-indolenine, 2,3,3,5-tetramethylindolenine, 2,3,3-trimethyl-5-chloroindolenine, 2,3,3-trimethyl-5-methoxy-indolenine, 1,3,3-trimethyl- 2-methylene-2,3-dihydroindole, 1-ethyl-3,3-dimethyl- 2-methylene-2,3-dihydroindole, 1-acetoxyethyl- 3,3-dimethyl-2-methylene-2,3-dihydroindole, 1,3,3,5-tetramethyl-2-methylene-2,3-dihydroindole, 1,3,3-trimethyl- 5-chloro-2-methylene-2,3-dihydroindole, 1,3,3-trimethyl- 5-methoxy-2-methylene-2,3-dihydroindole, 9,9,9a-trimethyl-2,3,9, 9a-tetrahydrooxazolo-[3,2a]-indole, 7,9,9,9a-tetramethyl-2, 3,9,9a-tetrahydrooxazolo[ 3,2a]-indole, 5-chloro-9,9,9a-trimethyl-2,3,9,9a-tetrahydrooxazolo-[ 3,2a]-indole.

Examples of suitable aromatic amines of the general formula IX are dimethylaniline, diethylaniline, dibutylaniline, N-methyl-N-hydroxyethyl-aniline, N-ethyl-N-hydroxyethyl-aniline, N-butyl-N-hydroxyethyl-aniline, N-methyl-N-acetoxyethyl-aniline, N-ethyl-N-acetoxyethylaniline, N-methyl-N-cyanoethyl-aniline, N-ethyl-N-cyanoethyl-aniline, N-methyl-N-benzylaniline, N,N-dibenzylaniline, N,N-dicyanoethyl-aniline, N,N-dihydroxyethyl-aniline, 3-methyl-N,N-dimethyl-aniline, 3-chloro-N,N-dimethylaniline, 3-methyl-N,N-diethylaniline, 3-chloro-N,N-diethyl-aniline, 3-acetylamino-N,N-diethyl-aniline, 3-ureido-N,N-diethyl-aniline, 1-ethyl- 2,2,4-trimethyl-tetrahydroquinoline, 1-hydroxyethyl- 2,2,4-trimethyl-tetrahydroquinoline, 1-ethyl-2,2,4,7-tetramethyl-tetrahydroquinoline, 2-methyl-2,3-dihydroindole, 2,5-dimethyl-N,N-dimethyl-aniline, 2,5-dimethoxy-N,N-dimethyl-aniline.

Examples of pyrazolone compounds of the general formula XI are 3-methyl-pyrazol-5-one, 1-amidino-3-methyl-pyrazol- 5-one, 1-phenyl-3-methyl-pyrazol-5-one, 1-(2-sulpho-phenyl)-3-methyl-pyrazol-5-one, 1-(3-sulphophenyl)-3-methyl-pyrazol-5-one, 1-(4-sulpho-phenyl)-3-methylpyrazol- 5-one, 1-(2-chloro-4-sulpho-phenyl)-3-methylpyrazol- 5-one, 1-(2-chloro-5-sulpho-phenyl)-3-methylpyrazol- 5-one, 1-(2,5-dichloro-4-sulpho-phenyl)-3-methyl-pyrazol-5-one, 1-(2-chloro-phenyl)-3-methylpyrazol- 5-one, 1-(3-chloro-phenyl)-3-methyl-pyrazol-5-one, 1-(4-chloro-phenyl)-3-methyl-pyrazol-5-one, ethyl 1-phenyl-pyrazol-5-one-3-carboxylate.

Examples of heterocyclic amines of the formula XIII are 2-amino-thiazole, 3-amino-isothiazole, 2-amino-benzothiazole, 2-amino-6-methoxy-benzothiazole, 3-amino-1,2,4-triazole, 3-amino-1,2,4-triazole-5-carboxylic acid, 1-phenyl-3,5-diamino-1,2,4-triazole, 2-amino-1,3,4-thiadiazole, 2-amino-5-dimethylamino-1,3,4-thiadiazole, 2-amino-5-diethylamino-1,3,4-thiadiazole, 2-amino-5-diisopropylamino-1,3,4-thiadiazole.

Examples of indole compounds of the general formula XV are 2-methyl-indole, 1,2-dimethyl-indole, 1-ethyl-2-methyl-indole, 2-phenyl-indole, 1-methyl-2-phenyl-indole, 1-methyl-2-phenyl-5-chloro-indole, 1-methyl-2-phenyl-5-methoxy-indole.

Example 1

173 g of 1,3,3-trimethyl-2-methylene-2,3-dihydroindole, 123 g of p-anisidine and a solution of 73 g of sodium nitrite in 300 ml of water were initially introduced into a pressure vessel, and $CO_2$ is injected up to a pressure of 50 bar. The temperature rises to 35° C., and the pressure drops. By further injection of $CO_2$, a pressure of 50 bar is maintained. The mixture is stirred at 35°–40° C. for 3 hours, and the pressure vessel is then let down to atmospheric pressure. The weakly alkaline suspension of the colour base is filtered off with suction, washed until neutral and dried to give 301.2 g of the colour base of the formula:

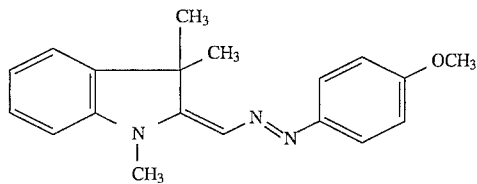

Melting point: 147°–150° C.

The colour base can be methylated in a known manner to give a cationic dyestuff which produces a golden yellow dyeing on polyacrylonitrile which has high light fastness.

Colour bases are also obtained in high yields by using equimolar amounts of aniline, p-toluidne, o-anisidine, o-toluidine or p-chloroaniline instead of p-anisidine.

Valuable colour bases are likewise obtained by using 1,3,3,5-tetramethyl-2-methylene-2,3-dihydroindole, 1,3,3-trimethyl- 5-chloro-2-methylene-2,3-dihydroindole, 1,3,3-trimethyl- 5-methoxy-2-methylene-2,3-dihydroindole or 1,3,3-trimethyl-5-phenoxy-2-methylene-2,3-dihydroindole instead of the coupling component used there.

Example 2

In a pressure vessel of 1 l capacity, 123 g of p-anisidine, 121 g of dimethylaniline and 73 g of sodium nitrite, dissolved in 300 ml of water, are stirred at room temperature. The autoclave is sealed, and $CO_2$ is injected up to a pressure of 50 bar. The reaction mixture is heated to 40° C., as a result of which the $CO_2$ pressure drops, which is then maintained at a constant pressure of 50 bar by further injection of $CO_2$. The mixture is stirred at 40° C. for 3 hours, the reaction vessel is cooled and let down to atmospheric pressure. The suspension of the azo dyestuff is then filtered off with suction, washed until neutral and dried to give 247 g of 4-methoxy-4'-dimethylaminoazobenzene.

The dyestuff can be used in sublimation transfer printing.

Valuable dyestuffs are likewise obtained by using p-toluidine, o-anisidine, o-toluidine or aminoresorcinol dimethyl ether instead of p-anisidine.

Valuable dyestuffs are likewise obtained with diethylaniline, dibutylaniline, methylhydroxyethylaniline or 3-methyl-N-ethyl-N-benzylaniline.

Example 3

216 g of 1,3-diaminobenzene are stirred in a pressure vessel with a solution of 90 g of sodium nitrite in 300 ml of water. $CO_2$ is injected up to a pressure of 50 bar, the reaction mixture is heated to 40° C. and stirred at 40° C. for 2 hours. After cooling, it is let down to atmospheric pressure, and the brown dyestuff suspension is filtered off to give 239.8 g of a dyestuff which dyes paper from an acid solution in brown hues.

A similar result is obtained by using 2,4-diaminotoluene instead of 1,3-diaminobenzene or using a mixture of the two amines.

Example 4

174 g of 1-phenyl-3-methylpyrazol-5-one, 107 g of p-toluidine and a solution of 73 g of sodium nitrite in 300 ml of water are stirred in an autoclave at room temperature, and $CO_2$ is injected up to a pressure of 50 bar. The reaction vessel is heated to 40° C., and the mixture is stirred at 40° C. for 2 hours. After cooling, the reaction vessel is let down to atmospheric pressure, and the dyestuff suspension is filtered off with suction, washed until neutral and dried to give 197 g of the dyestuff of the formula

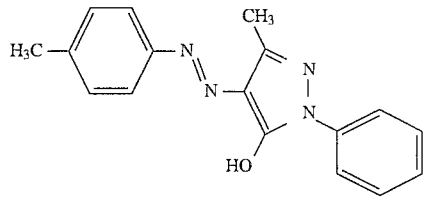

(m.p.: 112°–115° C.) which is suitable for the dyeing of poly(methyl methacrylate).

Example 5

208.5 g of 1-(2-chlorophenyl)-3-methylpyrazol-5-one, 107 g of p-toluidine and a solution of 73 g of sodium nitrite in 300 ml of water are placed into a pressure vessel, $CO_2$ is injected up to a pressure of 50 bar, and the temperature is increased to 40° C. After stirring at 40° C. for 2 hours, the reaction vessel is cooled and let down to atmospheric pressure. The dyestuff has solidified to a hard melt, it is comminuted, stirred in water, filtered off with suction, washed until neutral and dried to give 241.3 g of the dyestuff of the formula

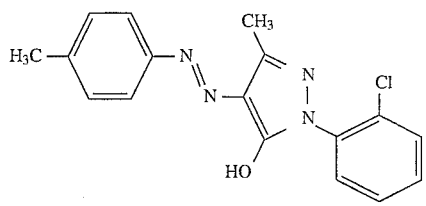

(m.p.: 89°–91° C.) which produces a yellow dyeing on poly(methyl methacrylate).

Example 6

84 g of 3-amino-1,2,4-triazole, 149 g of N,N-diethylaniline and a solution of 73 g of sodium nitrite in 300 ml of water are mixed in an autoclave, and CO$_2$ is injected up to a pressure of 50 bar. The reaction mixture is heated to 40° C., stirred at 40° C. for 2 hours, the autoclave is cooled, let down to atmospheric pressure, and the suspension of the colour base is filtered off with suction. The colour base is washed until neutral and dried to give 147.8 g of the colour base of the formula

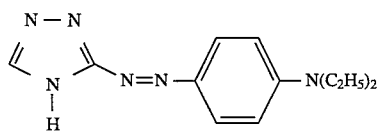

(m.p.: 187°–188° C.).

If the colour base is methylated in a known manner with dimethyl sulphate, a dyestuff is obtained which produces a red dyeing on polyacrylonitrile fibres which has high light fastness.

The procedure of this example is repeated, using an equimolar amount of N-ethyl-N-benzyl-m-toluidine instead of diethylaniline, to give a likewise valuable colour base.

Example 7

149 g of N,N-diethylaniline, 70.0 g of 1-phenylguanazole, 95 g of sodium nitrite, 100 g of water and 200 g of methanol are stirred in a pressure vessel, and CO$_2$ is injected up to a pressure of 65 bar. The mixture is first stirred at room temperature for 1 hour and then heated at 40° C. for 2 hours. After the major portion of the methanol has been distilled off, a resin is obtained which crystallizes after the addition of 20 ml of conc. hydrochloric acid. The yield is 97 g of a mixture of the azo base with the hydrochloride. The hydrochloride was separated off by boiling the mixture with ethanol, and the remaining colour base was recrystallized from 100 ml of dimethylformamide to give 43.4 g of the colour base of the formula

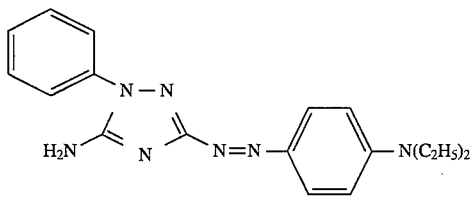

(m.p.: 235°–238° C.).

If dimethyl-m-toluidine is used as the coupling component instead of diethylaniline, a colour base is likewise obtained which melts at 281°–285° C.

Example 8

197 g of N-methyl-N-benzylaniline, 109.2 g of 3-amino-1,2,4-triazole, 94.9 g of sodium nitrite, 100 g of water and 200 g of methanol are mixed in a pressure vessel at room temperature with stirring. CO$_2$ is injected up to a pressure of 65 bar, the mixture is stirred at 25° C. for 1 hour and at 40° C. for 2 hours. During this reaction, the pressure of 65 bar is maintained by further injection of carbon dioxide. Overall, 351 g of carbon dioxide are absorbed. The reaction vessel is then cooled to room temperature and let down to atmospheric pressure. The suspension of the colour base is filtered off with suction, washed until neutral and dried. Yield 264.2 g; m.p.: 144°–146° C. The colour base of the formula

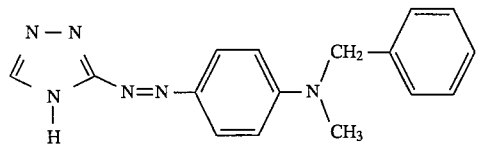

can be methylated with dimethyl sulphate to give a cationic dyestuff which produces red shades on polyacrylonitrile which have high light fastness.

Example 9

In an autoclave of 1,000 ml capacity, a solution of 94.9 g of sodium nitrite in 100 g of water and 200 g of methanol are added to 211 g of N-ethyl-N-benzylaniline and 109.2 g of 3-amino-1,2,4-triazole, and carbon dioxide is injected at 25° C. up to a pressure of 65 bar. The mixture is stirred at 25° C. for 1 hour and at 40° C. for 2 hours, during which a maximum pressure of 75 bar is obtained by further injection of CO$_2$. Overall 358 g of CO$_2$ are injected. The reaction vessel is cooled and let down to atmospheric pressure. The suspension of the colour base is filtered off with suction, washed until neutral and dried. Yield: 278.4 g; m.p.: 147°–150° C.

The colour base content of the formula

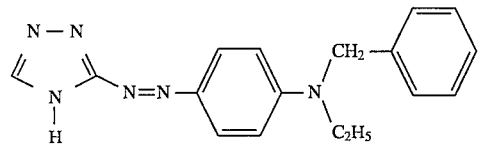

in the crude product is 74.5%. Methylation of this colour base gives a cationic dyestuff which produces red shades on polyacrylonitrile fibres which have high light fastness.

Example 10

197 g of N-methyl-N-benzylaniline, 128 g of 5-amino-1,2,4-triazol-2-carboxylic acid and 73 g of sodium nitrite, dissolved in 300 ml of water, are initially introduced into a pressure vessel, and CO$_2$ is injected at 25° C. up to a pressure of 65 bar. The mixture is stirred at 25° C. for 1 hour and at 40° C. for 2 hours, and a pressure of 65 bar is maintained by further injection of CO$_2$. Overall 230 g of CO$_2$ are absorbed. The reaction vessel is cooled and let down to atmospheric pressure, and the dyestuff formed is filtered off with suction, washed and dried in vacuo to give 218.9 g of the dyestuff of the formula

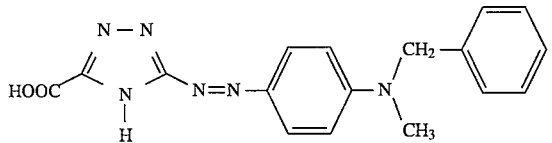

(m.p.: >250° C.).

Example 11

183 g of N-methyl-diphenylamine, 184.8 g of 3-amino-1,2,4-triazole and 151.8 g of sodium nitrite, dissolved in 300 ml of water, are initially introduced into an autoclave, $CO_2$ is injected at 25° C. up to a pressure of 50 bar, and the mixture is stirred at room temperature for 6 hours. The reaction vessel is let down to atmospheric pressure, and the colour base formed of the formula

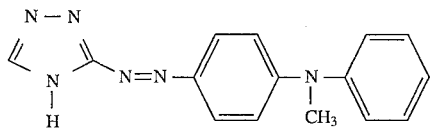

is isolated by filtering off with suction, washing until neutral and drying. Yield: 213.9 g; m.p.: 173°–175° C.

Example 12

In an autoclave, 112.5 g of N-ethyl-N-benzyl-3-methylaniline and 54.6 g of 3-amino-1,2,4-triazole are mixed with a solution of 47.5 g of sodium nitrite in 50 ml of water and 100 ml of methanol with stirring, and carbon dioxide is injected up to a pressure of 60 bar. The temperature is then increased to 40° C., and the mixture is stirred at 40° C. for 5 hours under a $CO_2$ pressure of 60 bar. The mixture is then cooled to room temperature, the pressure vessel is let down to atmospheric pressure, the solution is decanted, and the melt of the colour base is comminuted by grinding with ice. The product is filtered off with suction, washed until neutral and dried to give 157.8 g of the colour base of the formula

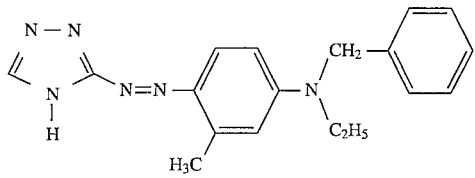

Methylation of this colour base with dimethyl sulphate gives a cationic dyestuff which produces red shades on polyacrylonitrile which have high light fastness.

Example 13

112.5 g of N-ethyl-N-benzyl-3-methylaniline, 54.6 g of 3-aminotriazole, 47.5 g of sodium nitrite, dissolved in 50 ml of water, and 300 ml of propanediol are combined in an autoclave with stirring, and carbon dioxide is injected up to a pressure of 40 bar. The mixture is stirred at 30° C. for 24 hours, and the reaction vessel is let down to atmospheric pressure. This gives 571.2 g of a solution in which the starting components Can be detected by thin-layer chromatogram only in traces. 126.1 g of dimethyl sulphate are added to this solution at room temperature, and the mixture is stirred at room temperature for 3 hours. The unmethylated colour base can still be detected in the thin-layer chromatogram. 42 g of dimethyl sulphate are added to the mixture, which is stirred at room temperature for 21 hours and after the addition of another 21 g of dimethyl sulphate and stirring at room temperature for 6 hours only traces of the colour base can still be detected. The reaction mixture is then heated to 70° C. and maintained at this temperature for 1 hour to bring the methylation to completion and destroy the excess dimethyl sulphate. The dark red solution is then filtered. The solution of the dyestuff of the formula

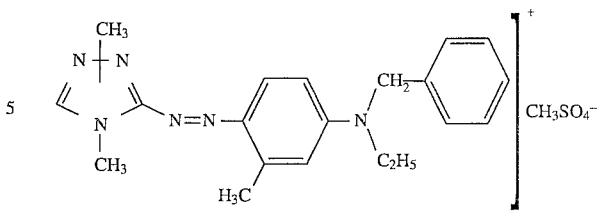

is suitable for producing red shades on polyacrylonitrile which have high light fastness.

Example 14

225 g of N-ethyl-N-benzyl-3-methylaniline, 109.2 g of 3-amino-1,2,4-triazole, 94.9 g of sodium nitrite, dissolved in 100 ml of water, and 200 g of isopropanol are combined in an autoclave, and carbon dioxide is injected at 25° C. up to a pressure of 65 bar. The mixture is stirred at 25° C. for 1 hour and at 40° C. for 2 hours. The reaction vessel is then cooled, let down to atmospheric pressure, the colour base formed of the formula given in Example 12 is filtered off with suction, washed until neutral and dried in vacuo. Yield: 251.1 g.

The same colour base is obtained in a yield of 218 g if isoamyl alcohol is used as the solvent instead of isopropanol.

Example 15

18 g of 2-amino-6-methoxybenzothiazole and 16 g of N-ethyl-N-(2-hydroxyethyl)aniline are placed into a pressure vessel together with a solution of 7 g of sodium nitrite in 30 ml of water and 40 g of methanol, and $CO_2$ is injected up to a pressure of 65 bar. Stirring at room temperature is continued for 21 hours, and the pressure vessel is then let down. The colour base formed is filtered off with suction, washed until neutral and then freed from the remainders of the starting materials by washing with ice-cold methanol to give 15.9 g of the colour base of the formula:

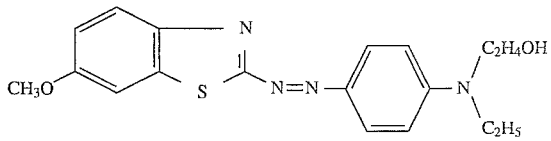

Example 16

173 g of 1,3,3-trimethyl-2-methylene-2,3-dihydroindole, 123 g of p-anisidine, 124 g of isoamyl nitrite and 300 ml of water are initially introduced into a pressure vessel, and $CO_2$ is injected up to a pressure of 50 bar. The autoclave is heated up to 40° C., and the pressure is kept constant at 50 bar by further injection of $CO_2$. The mixture is stirred at 35°–40° C. for 3 hours, and the pressure vessel is then let down to atmospheric pressure. The colour base is separated off and dried to give 262.0 g of a colour base whose formula is given in Example 1. M.p.: 133°–136° C.

Example 17

In a pressure vessel, 16.8 g of 3-amino-1,2,4-triazole, 45.0 g of N-ethyl-N-benzyl-3-methylaniline, 30.4 g of amyl nitrite, 80 ml of methanol and 40 ml of water are added, and $CO_2$ is injected up to a pressure of 53.5 bar. The autoclave is heated to 40° C., and the temperature is maintained at 34°–40° C. for 3 hours and the pressure at 50–55 bar by further injection of $CO_2$. The reaction vessel is then cooled, let down to atmospheric pressure, and the methanol is distilled off. Crystallization of the residue is induced with saturated common salt solution and a small amount of hydrochloric acid, further purified with methylene chloride and dried to give 64.4 g of a colour base whose formula is given in Example 12. M.p.: 80°–94° C.

Example 18

In a pressure vessel, 34.5 g of 2-chloro-4-nitroaniline, 38.4 g of N-ethyl-N-dimethylaminoethylaniline, 30.4 g of amyl nitrite, 80 ml of methanol and 40 ml of water are combined, and $CO_2$ is injected up to a pressure of 50 bar. The reaction mixture is heated to 34°–40° C. and stirred at this temperature for 3 hours. During this time, the pressure of 50 bar is maintained by further injection of $CO_2$. The reaction mixture is then cooled, and the autoclave is let down to atmospheric pressure. The methanol is distilled off, and the residue is poured into 1 l of water. After stirring overnight, the colour base is isolated and dried. Yield: 57.1 g.

Example 19

In a pressure vessel, 36.0 g of 2-amino-6-methoxybenzothiazole, 33.0 g of N-ethyl-N-2-hydroxyethylaniline, 30.4 g of amyl nitrite and 60 ml of water are added, and $CO_2$ is injected up to a pressure of 50 bar. The reaction mixture is then heated to 34°–40° C. and stirred at this temperature and a $CO_2$ pressure of 50 bar for 3 hours. The reaction mixture is then cooled, let down to atmospheric pressure and poured into 1 l of water. The oily residue is taken up in methylene chloride and evaporated to dryness in a rotary evaporator to give 44.9 g of a colour base whose formula was given in Example 15.

Example 20

27.9 g of anthranilic acid, 34.8 g of 1-phenyl-3-methyl-5-pyrazolone, 31.2 g of amyl nitrite, 80 ml of methanol and 40 ml of water are mixed in an autoclave, and $CO_2$ is injected up to a pressure of 50 bar. The reaction mixture is then heated to 34°–40° C. and a $CO_2$ pressure of 50 bar is maintained during the three-hour reaction time. The autoclave is then cooled and let down to atmospheric pressure. The reaction mixture is poured into 1 l of water and, after stirring overnight, filtered off with suction. The yield of the dyestuff of the formula

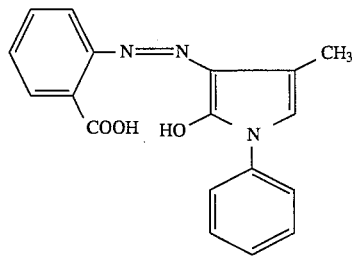

after drying is 56.9 g.

Example 21

In a pressure vessel, 27.9 g of anthranilic acid, 34.8 g of 1-phenyl-3-methyl-5-pyrazolone, 61.0 g of ethoxypropanol, 59 ml of water and 31.2 g of amyl nitrite are combined, and $CO_2$ is injected up to a pressure of 50 bar. The reaction mixture is heated to 40° C. and stirred for 3 hours at this temperature, while maintaining a constant $CO_2$ pressure of 50 bar. After cooling, the reaction vessel is let down to atmospheric pressure, and the reaction mixture is transferred to a three-necked flask. A 38% strength paste of the 1:1 chromium complex of the coupling product of 4-sulphoanthranilic acid onto phenylmethylpyrazolone (223.0 g) is added to the mixture. It is then made up to 1000 ml with 550 g of a 50:35 ethoxypropanol/water mixture, and the solution is brought to a pH of 7 with lithium hydroxide. The solution is then heated at 70° C. for 2 hours, while keeping the pH constant at 7 by adding lithium hydroxide. The solution is then cooled and filtered. The solution is suitable for the dyeing of leather.

Example 22

40 g of 2-amino-5-diisopropylamino-1,3,4-thiadiazole, 24.2 g of N,N-dimethylaniline, 30.4 g of isoamyl nitrite, 40 ml of water and 80 ml of methanol are mixed in a pressure vessel and $CO_2$ is introduced until a pressure of 50 bar is reached. The mixture is heated to 40° C. and stirred at this temperature for 3 hours while maintaining a constant pressure. After releasing the pressure the dyestuff base of the formula

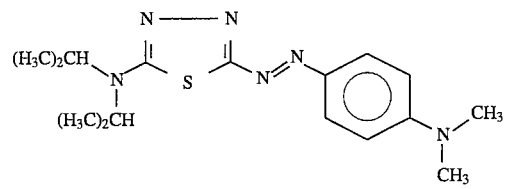

is separated off and dried. Yield: 63 g, m.p.: 168°–170° C. The dyestuff base is methylated in known manner to give a cationic dyestuff which colours polyacrylonitrile in very lightfast blue shades.

Example 23

20 g of 2-amino-5-diisopropylamino-1,3,4-thiadiazole, 27.6 g of 2-amino-3-methyl-1,3-benzthiazolium methosulphate, 12 g of isoamyl nitrite, 40 ml of water and 80 ml of methanol are mixed in an autoclave, subjected to a $CO_2$ pressure of 50 bar and heated to 40° C. The mixture is stirred for 3 hours at this temperature under a constant pressure. Then the pressure is released from the autoclave, the methanol is distilled off and the dyestuff base of the formula

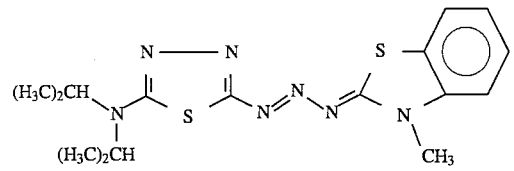

is discharged onto water and filtered off with suction. After drying the yield is 28.5 g, m.p.: 195°–198° C. By methylation with dimethyl sulphate a cationic dyestuff is obtained which colours polyacrylonitrile in a lightfast red shade.

The reaction is supposed to proceed according to the following scheme:

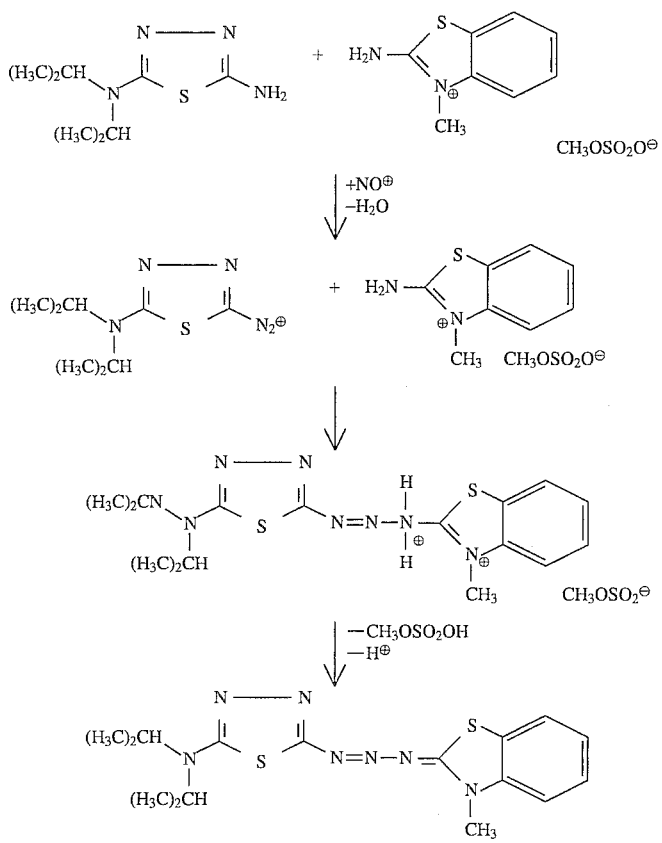

Similarly valuable dyestuffs are obtained if the methylated quaternary salts of 3-aminotriazole, 2-aminothiazole or 2-amino- 5-diisopropylamino-1,3,4-thiadiazole are used instead of 2-amino- 3-methyl-1,3-benzthiazolium methosulphate for the synthesis of the dyestuff base.

Example 24

16.8 g of 3-amino-1,2,4-triazole, 34.6 g of 3-amino-5-methyl- 2-phenylpyrazole and 14 g of sodium nitrite in 80 ml of water are mixed in a pressure vessel and $CO_2$ is introduced until a pressure of 50 bar is reached. After heating the mixture to 40° C. it is stirred at this temperature and the starting pressure for three hours. After cooling to room temperature the pressure is released from the vessel and the dyestuff base of the formula

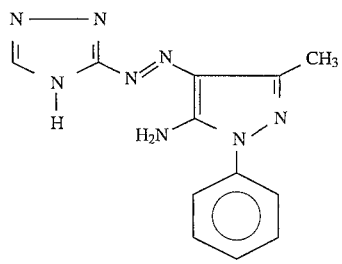

is isolated. After drying the yield is 37.2 g, m.p.: 61°–64° C. The dyestuff base is methylated with dimethyl sulphate to give a cationic dyestuff which colours polyacrylonitrile in lightfast yellow shades.

Example 25

34.4 g of 1,3,3-trimethyl-2-methylene-2,3-dihydroindole, 24.6 g of p-anisidine, 30.4 g of isoamyl nitrite, 40 ml of water and 80 ml of methanol are mixed in a pressure vessel and 200 g of $CO_2$ are condensed therein at 0° C. under a pressure of 65 bar. The pressure vessel is closed and the mixture is stirred for 10 hours under the vapour pressure of the $CO_2$. The autoclave is depressurised and allowed to reach room temperature. After removing the methanol by distillation the dyestuff base of the formula mentioned in Example 1 is precipitated in a yield of 36.1 g.

Example 26

16.8 g of 3-aminotriazole, 45 g of N-ethyl-N-benzyl-3-methylaniline, 30.4 g of amyl nitrite, 40 ml of water and 80 ml of methanol are mixed in a pressure vessel and $CO_2$ is introduced until a pressure of 50 bar is reached. The temperature is increased to 100° C., during which the pressure increases to 60 bar. At this temperature the mixture is stirred for three hours while maintaining a pressure of 55 bar. After cooling and releasing the pressure from the autoclave the dyestuff base of the formula mentioned in Example 12 is isolated. Yield: 62.7 g.

Example 27

The reaction described in Example 16 is repeated with the sole difference that the pressure is released from the vessel after only 10 minutes. The dyestuff base of the formula mentioned in Example 1 is obtained in a yield of 171 g.

It will be understood that the specification and examples are illustrative but not limitative of the present invention and that other embodiments within the spirit and scope of the invention will suggest themselves to those skilled in the art.

What is claimed is:

1. A process for the preparation of dyestuffs of the general formula

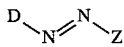

in which
   D is the radical of a heterocyclic diazo component selected from the group consisting of substituted and unsubstituted, benzo-fused and non-benzo-fused thiazols, isothiazols, thiadiazols, oxazols, imidazols and triazols and
   Z is the radical of a substituted or unsubstituted $C_6$–$C_{10}$-arylamino group or is the radical of the formula

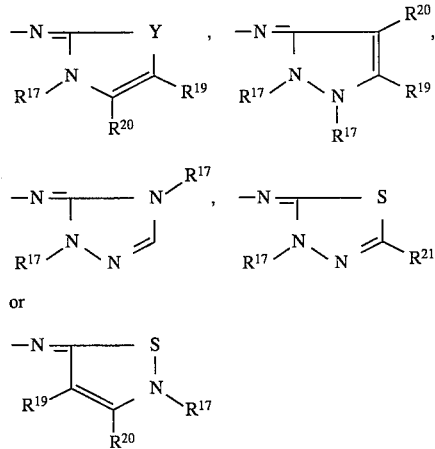

in which
   Y represents —S—, —O— or

$R^{17}$ represents hydrogen, unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen, unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy,
   $R^{19}$ and $R^{20}$ either represent hydrogen or together represent the remaining members of a fused benzene ring and
   $R^{21}$ represents $C_1$–$C_4$-(di)alkylamino, $C_6$–$C_{10}$-(di)arylamino, $C_1$–$C_4$-alkyl-$C_6$–$C_{10}$-arylamino, morpholino, piperidino, piperazino, pyrrolidino, $C_1$–$C_4$-alkylmercapto or $C_6$–$C_{10}$-arylmercapto,
in which a diazo component of the formula

and a component of the formula

wherein $Z_1$ is a radical of a substituted or unsubstituted $C_6$–$C_{10}$-arylamino group or a radical of the formulae

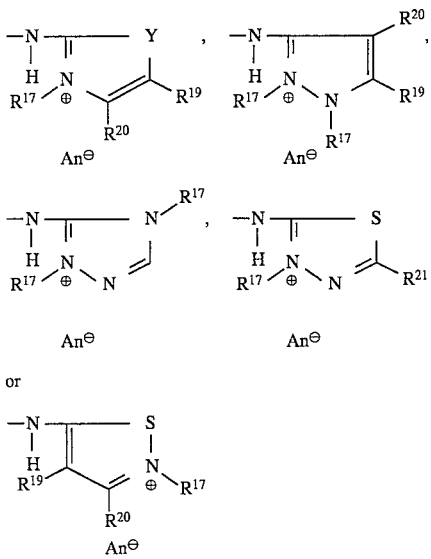

in which
   Y, $R^{17}$, $R^{19}$, $R^{20}$ and $R^{21}$ have the above given meaning and
   $An^{\ominus}$ represents an anion selected from the series comprising $Cl^{\ominus}$, $CH_3OSO_2O^{\ominus}$, $I^{\ominus}$, $Br^{\ominus}$, $CH_3COO^{\ominus}$,
and
   the substitutents for the substituted aromatic diazo component, the substituted heterocyclic diazo component, the aryl part of the substituted $C_6$–$C_{10}$-arylamino groups in the definition of Z and $Z_l$, the heterocyclyl part of the heterocyclylimino group, the hetaryl part of the hetarylamino group, or the substituted carbocyclic rings are concerned, being selected from the group consisting of $C_1$–$C_4$-alkyl, $C_6$–$C_{10}$-aryl, $C_1$–$C_4$-alkoxy, $C_1$–$C_4$-alkoxycarbonyl, $C_1$–$C_4$-alkylcarbonyloxy, cyano, $C_1$–$C_4$-(di)alkylamino, $C_1$–$C_4$-(di)alkylaminocarbonyl, $C_1$–$C_4$-alkylcarbonylamino, hydroxy, halogen, $C_1$–$C_4$-alkylcarbonyl, $C_1$–$C_4$-alkylsulphonyl, $C_1$–$C_4$ -(di)alkylaminosulphonyl, $C_1$–$C_4$-alkylsulphonylamino, $C_1$–$C_4$-alkoxysulphonyl, $C_1$–$C_4$-alkylsulphonyloxy, nitro, $C_6$–$C_{10}$-(di)arylamino, $C_1$–$C_4$-alkyl-$C_6$–$C_{10}$ -arylamino, phenylsulphonyl, phenylazo, benzothiazolyl, 1,2,4-oxadiazolyl, morpholino, piperidino, piperazino, pyrrolidino, $C_1$–$C_4$-alkylmercapto and $C_6$–$C_{10}$-arylmercapto and as far as the amino part of the substituted $C_6$–$C_{10}$-arylamino group in the definition of Z and $Z_1$ is concerned, it is unsubstituted or substituted by substituted or unsubstituted $C_1$–$C_8$-alkyl, $C_2$–$C_4$-alkylen or substituted or unsubstituted $C_1$–$C_4$ -alkyl-$C_6$–$C_{10}$-aryl,
   are reacted in an aqueous medium with a nitrite selected from the group consisting of alkali nitrite, $C_1$–$C_5$-alkyl nitrite, glycol nitrite or polyol nitrite in the presence of $CO_2$ at a pressure of 5–100 bar at a temperature of 0°–125° C.

2. A process according to claim 1, in which the reaction is carried out during a time of 10 minutes to 24 hours.

3. A process according to claim 1, in which the reaction is carried out at a temperature of 0°–100° C.

4. A process according to claim 1, in which
   Z is the radical of the formula

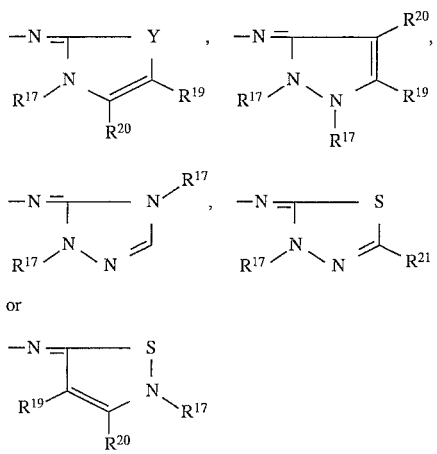

in which

Y represents —S—, —O— or

$R^{17}$ represents hydrogen, unsubstituted $C_1$–$C_8$-alkyl or $C_1$–$C_8$-alkyl which is substituted by hydroxy, halogen, cyano, $C_1$–$C_4$-alkoxy, carboxyl, $C_1$–$C_4$-(di)alkylaminocarbonyl, $C_1$–$C_4$-alkoxycarbonyl or $C_1$–$C_4$-alkylsulphonyl or represents $C_2$–$C_4$-alkylen, unsubstituted phenylmethyl, unsubstituted phenylethyl or phenylmethyl or phenylethyl which in each case is substituted by halogen, cyano, $C_1$–$C_4$-alkyl or $C_1$–$C_4$-alkoxy, $R^{19}$ and $R^{20}$ either represent hydrogen or together represent the remaining members of a fused benzene ring and $R^{21}$ represents $C_1$–$C_4$-(di)alkylamino, $C_6$–$C_{10}$-(di)arylamino, $C_1$–$C_4$-alkyl-$C_6$–$C_{10}$-arylamino, morpholino, piperidino, piperazino, pyrrolidino, $C_1$–$C_4$-alkylmercapto or $C_6$–$C_{10}$-arylmercapto and $Z_1$ is the radical of the formulae

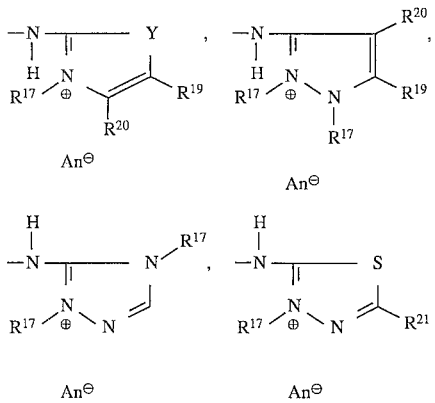

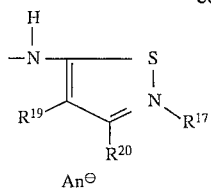

in which

Y, $R^{17}$, $R^{19}$, $R^{20}$ and $R^{21}$ have the above given meaning and $An^{\ominus}$ represents an anion selected from the series comprising $Cl^{\ominus}$, $CH_3OSO_2O^{\ominus}$, $I^{\ominus}$, $Br^{\ominus}$, $CH_3COO^{\ominus}$.

5. A process according to claim 1, in which a compound of the general formula

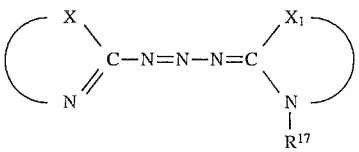

in which

X represents the remaining members of a thiazole, benzothiazole, 1,2,4-triazole or 1,3,4-thiadiazole, $X_1$ represents the remaining members of a thiazoline, isothiazoline, benzothiazoline, 1,2,4-triazoline, 1,34-thiadiazoline radical, $R^{17}$ represents $C_1$–$C_4$-alkyl, which can be unsubstituted or substituted by cyano, $C_1$–$C_4$-(di)alkylaminocarbonyl, hydroxyl, $C_1$–$C_4$-alkoxy, carboxyl, $C_1$–$C_4$-alkoxycarbonyl, $C_1$–$C_4$-alkylsulphonyl are prepared by reacting a heterocyclic amine of the formula

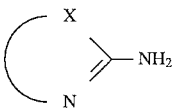

in which

X has the above given meaning with a heterocyclic ammonium compound of the formula

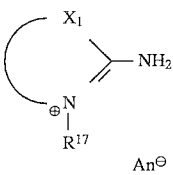

in which $X_1$ and $R^{17}$ have the above given meaning and $An^{\ominus}$ represents an anion selected from the series comprising $Cl^{\ominus}$, $CH_3OSO_2O^{\ominus}$, $I^{\ominus}$, $Br^{\ominus}$, $CH_3COO^{\ominus}$.

6. A process according to claim 1, in which the reaction is carried out at 25–65 bar.

7. A process according to claim 1, in which the reaction is carried out at 0°–70° C.

8. A process according to claim 1, in which the reaction is carried out at 30°–40° C.

9. A process according to claim 1, in which the nitrite is sodium nitrite, potassium nitrite, methyl nitrite, isopropyl nitrite, amyl nitrite, glycol nitrite and pentaerythritol nitrite or diethylene glycol nitrite.

10. A process according to claim 1, in which the reaction is carried out in an aqueous medium.

11. A process according to claim 2, in which the reaction is carried out in a mixture of water and methanol.

12. A process according to claim 1, in which the reaction is carried out in a mixture of water and methanol.

* * * * *